(12) United States Patent
Liversidge (10) Patent No.: US 8,172,810 B2
(45) Date of Patent: May 8, 2012

(54) MEDICAL NEEDLE SAFETY DEVICES (75) Inventor: Barry Peter Liversidge, Colchester (GB)

(73) Assignee: Barry Peter Liversidge, Essex (GB)

( * ) Notice: Subject to any disclaimer, the term of this patent is extended or adjusted under 35 U.S.C. 154(b) by 258 days.

(21) Appl. No.: 11/722,983

(22) PCT Filed: Jan. 9, 2006

(86) PCT No.: PCT/GB2006/050005
§ 371 (c)(1),
(2), (4) Date: Jun. 27, 2007

(87) PCT Pub. No.: WO2006/072807
PCT Pub. Date: Jun. 13, 2006

(65) Prior Publication Data
US 2008/0103453 A1   May 1, 2008

(30) Foreign Application Priority Data
Jan. 8, 2005 (GB) .................................. 0500366.0

(51) Int. Cl.
*A61M 5/32* (2006.01)
(52) U.S. Cl. ........................................ 604/198; 604/192
(58) Field of Classification Search .......... 604/192–198, 604/110, 187
See application file for complete search history.

(56) References Cited

U.S. PATENT DOCUMENTS
2006/0167411 A1* 7/2006 Weston et al. ................ 604/110

FOREIGN PATENT DOCUMENTS
EP 0268445 1/1991
EP 0467173 11/1995
WO WO 2004/071560 8/2004

* cited by examiner

*Primary Examiner* — Jackie Ho
*Assistant Examiner* — Imani Hayman
(74) *Attorney, Agent, or Firm* — Andrus, Sceales, Starke & Sawall, LLP (57) ABSTRACT

A safety device (10) for a medical needle (11) has a sleeve (28) defining an internally tapering forward portion (30) and a needle carrier (14) located within the sleeve (28) for axial movement relative to the forward portion (30). A locking member (23) is mounted on the needle carrier (14) and has a plurality of resiliently deformable fingers (25) bearing on the internal surface of the sleeve and slidable along the tapering forward portion (30) as the carrier moves relative thereto, so as to impart a force between the carrier (14) and forward portion (30) to restore those components to their initial position. A cam arrangement (33) turns the locking member (23) following initial axial movement between the carrier (14) and forward portion (30) so that the forward ends of the fingers drop behind abutments (35) provided at the rearward end of the forward portion, upon the carrier and forward portion returning to their initial positions. This then blocks further axial movement between those components (14, 30).

24 Claims, 12 Drawing Sheets

MEDICAL NEEDLE SAFETY DEVICES

CROSS REFERENCE TO RELATED APPLICATION

The present application is the U.S. national stage application of International Application PCT/GB2006/050005, filed Jan. 9, 2006, which international application was published on Jul. 13, 2006 as International Publication WO 2006/072807. The International Application claims priority of British Patent Application 05 00366.0, filed Jan. 8, 2005.

This invention relates to a safety device for a medical needle, to confer passive protection for a needle with which the device is associated. The invention also relates to a safety needle assembly and to an injection device incorporating such a safety needle assembly.

The safety device of this invention has been designed for use with a medical needle having a mount end and a sharp tip, intended for penetration of a human or animal body, or for other medical uses such as the penetration of a pierceable membrane or of an intravenous medication system. For convenience reference will be made herein solely to the penetration of a body, even though specific embodiments of this invention may be intended for other medical uses.

Throughout this specification, reference is made to the relative terms "forward" and "rearward"; "forward" and "forwardly" refer to the end of the device which is presented to a body when a medical procedure is to be performed (that is, the tip end of the needle) and the direction towards that end; and the terms "rearward" and "rearwardly" refer to the other end of the device (that is, the end of the device nearer a syringe with which the device may be used) and the direction towards that other end.

Fluids of various kinds may be administered to a body by means of a hollow needle in conjunction with a source of the required fluid. For example, such a needle may be associated with a syringe holding a liquid drug, the needle being used to penetrate the body at the site at which the drug is to be received. Equally, body fluids may be withdrawn by using a hollow needle which is used to penetrate the body until the tip is located at the site from which fluid is to be withdrawn.

A recognised hazard for clinicians and other persons using medical needles for the above described purposes is the risk of a so-called needle-stick injury—that is to say the accidental penetration of the clinician's skin by the needle. Prior to the use of the needle to supply a fluid to or to withdraw fluid from a body, this rarely presents much of a problem, though once the needle has been used on a body, there is a very much higher risk of a serious consequence for the clinician, or others associated with the disposal of a used needle. During use of the needle to penetrate the body tissues of a patient, the needle is likely to become contaminated with various organisms and should a needle-stick injury occur, these could infect the clinician or other person suffering the needle-stick injury.

There have been numerous proposals for protecting the sharp tip of a used needle, in order to reduce the risk of a needle-stick injury following use of the needle. Some proposals have actually increased the likelihood of such an injury by virtue of the action which must be performed to protect the tip, even if the risk thereafter is lessened. Despite all of the proposals which have previously been made, very few have achieved commercial success, nor has there been wide acceptance by the medical industry. Many proposals are somewhat complex and involve a significantly greater manufacturing cost, and so are unacceptable on economic grounds. Others are much more difficult to use as compared to an unprotected needle, and so are rejected by clinicians. Yet further proposals do not allow compliance with best practice protocols.

There is a significant demand for a protective device for use with a needle, and which allows a clinician or perhaps a patient (in the case of self-administration) to use the needle in much the same way as is done with an unprotected needle, but which can be manufactured economically and which provides a high degree of protection against needle-stick injury. In this connection, it is much preferred that the protection feature of the device operates fully automatically, without intervention by the user, to give a degree of protection to the needle tip before use, and after use wholly to prevent access to the needle tip other than by a determined attempt to override the protection. In this way, protection may be afforded not just to the user, but also to all others who could come into a risky situation with used needles, such as waste disposal operators, cleaners, and so on.

A device which protects a needle tip without a clinician having to perform any extra step on deliberately or accidentally withdrawing the needle from a body is usually referred to as a passive protection device. This may be contrasted with an active protection device, where an clinician is required to perform an extra step in order to protect a needle, following the withdrawal of the needle from a body. The requirement to perform an extra step leaves the needle unprotected for a longer period than with a passive protection device and further the performance of that extra step often exposes the user to a potentially hazardous situation, where needle-stick injuries can occur.

In earlier International Patent Publication No. WO 04/071560 there is described a passive protection device aimed at preventing needle stick injury to clinicians and others who may be involved directly or indirectly with the use and disposal of medical needles. The device of that earlier application has a spring defined by a plurality of fingers which operate on an external conical surface, to provide a force restoring a shield to an initial position where that shield protects a needle associated with the device. As access to the fingers can be obtained at any time, it is very easy to over-ride the protection afforded by the device and further the shield is only poorly located on the conical surface, so giving imprecise operation. A further disadvantage is that during storage of the device before use, the shield is displaced from its final protecting position, which thus requires the fingers to be resiliently deformed from their final position. The plastic material from which the fingers are made will acquire a "set" during an extended period of storage and so locking of the shield by the fingers in the final protecting position cannot reliably be assured.

The above problem has been addressed in EP 1535640 A1, by providing packaging for a safety device similar to that described in WO 04/071560 and which allows a user to set the device so as to be ready for use, as a syringe is connected thereto. This moves the fingers to a stressed position but allows long term storage of the device without the fingers being deformed, though it does mean the device cannot be supplied to a user, ready for use.

The present invention has been developed with the aim of providing a simple, easy to use and economically viable safety device for a medical needle, to give passive protection thereto, when performing an injection. The device of this invention may be used as an accessory for a medical needle attachable to a syringe or permanently fitted thereto, or may incorporate a medical needle as a part of the device, for connection to a syringe.

According to this invention, there is provided a safety device for a medical needle having a sharp tip, which device comprises:

an outer sleeve having an internal surface including a forward portion which tapers internally towards its forward end and a rearward portion defining an essentially parallel bore;

a carrier for a needle supported in the bore and arranged for axial movement with respect to the forward portion of the sleeve, the carrier and forward portion having an initial position where at least the tip of a carried needle is surrounded by the forward portion and further having an injecting position where a carried needle projects from the forward portion;

a locking member forwardly of the carrier and also arranged for axial movement with respect to the forward portion of the sleeve, the locking member having at least one resilient finger projecting forwardly within the sleeve, the locking member and forward portion also having an initial relative position where the forward end of the finger contacts the inner surface of the sleeve in the region of the junction between the forward and rearward portions thereof and on relative movement of the locking member and forward portion from their initial position, the finger is resiliently deformed inwardly thereby urging the locking member and carrier back to their initial positions;

at least one abutment formed between the forward and rearward portions of the sleeve, which abutment is out of angular alignment with the finger when the locking member and forward portion are in their initial position; and control means to turn the locking member during relative movement between the carrier and the forward portion from their initial position thereby bringing the forward end of the finger onto the tapering internal surface of the forward portion and into angular alignment with the abutment, such that when the carrier and forward portion return to their initial position, the forward end of the finger locates behind the abutment and so blocks subsequent movement.

The device of this invention uses a spring force to urge a protecting sleeve forwardly to cover a needle with which the device is associated, that spring force being generated by at least one finger sliding on a tapering surface. The carrier and locking member are disposed within the outer sleeve and so those components are inaccessible. Further, it becomes possible to taper the outer surface of the forward portion of the sleeve towards its forward end from which the needle projects when a medical procedure is to be performed, so giving the overall safety device a profile which makes it easier to handle and use in performing a procedure.

After performing an injection, the carrier and forward portion of the sleeve will end up at a protecting position where the abutment will block movement of the finger and so also of the carrier relative to the forward portion; that final protecting position may correspond axially to the initial position of the carrier and forward portion, whereby the needle tip is wholly surrounded.

Most preferably, the outer sleeve is generally tubular with a relatively thin wall. This allows the outer sleeve to have a substantially cylindrical rearward portion and a substantially conical forward portion the larger diameter end of which connects to the forward end of the rearward portion, with the or each abutment formed at the junction therebetween. In one embodiment, the carrier is mounted within the rearward portion of the sleeve for sliding movement with respect thereto, along the axis of the sleeve. In an alternative embodiment, the carrier is mounted within the rearward portion of the sleeve but is held against movement with respect thereto. In this alternative embodiment, the forward portion of the sleeve is slidably mounted within the rearward portion whereby the carrier and forward portion of the sleeve may move axially with respect to each other.

Advantageously, there is a plurality of, and preferably three, fingers equi-spaced about the axis of the sleeve, and a corresponding number of abutments so that there is one for each finger.

The control means may include, for each finger, a respective first cam surface formed internally within the sleeve and engageable by a second cam surface provided on the associated finger. At least one of each first and second cam surface should extend generally helically with respect to the axis of the sleeve whereby interaction between the first and second cam surfaces on relative movement of the locking member and forward portion from their initial position turns the locking member about the sleeve axis. Preferably, the first cam surfaces are formed within the forward portion of the sleeve and the second cam surfaces are defined by the forward ends of the fingers. This embodiment allows the locking member to start turning more or less as soon as the locking member has moved through only a small distance from its initial position, whereby the carrier will be locked in its final position on the return of the locking member and carrier, protecting the needle.

In a case where a medicament is to be drawn down from a vial into the syringe using the needle which will subsequently be used for performing the injection, it is advantageous if a safety device can be used for the draw-down procedure as well as for performing the injection. In this case, the safety device must allow exposure of the needle though to a lesser extent than were a medical procedure to be performed, followed by the return of the carrier and forward portion of the sleeve to the initial position without locking taking place. Thereafter, the safety device may be used to perform the medical procedure and following that, locking will take place so protecting the needle tip.

In order to allow such a procedure to be performed, the first and second cam surfaces of the control means may be spaced axially when the locking member is in its initial position, whereby the carrier and forward portion of the sleeve must move through that distance before the locking member is turned. The axial spacing of the cam surfaces may be selected to an appropriate distance to permit the performance of a draw-down procedure without the locking member being rotated.

In an alternative embodiment, the control means comprises interacting cam surfaces provided respectively on the carrier and the locking member and arranged to cause rotation of the locking member with respect to the carrier on forward movement of the carrier with respect to the locking member. The engagement of the forward ends of at least one finger with shoulders to each side of the abutment will resist such rotational movement until those forward ends have moved forwardly sufficiently to come clear of the shoulders. This will occur on forward movement of the carrier with respect to the forward portion of the sleeve, and thereafter the locking member will be rotated. Then, on subsequent return of the locking member to its initial axial position with respect to the forward portion, the forward ends of the fingers will engage the abutments and block subsequent relative movement of the carrier and the forward portion of the sleeve.

The carrier may have a forward-facing surface confronting a rearward-facing surface of the locking member, said interacting cam surfaces being provided on the forward- and rearward-facing surfaces. The rearward-facing surface of the locking member preferably is formed at the rearward end of the locking member and the fingers project forwardly from that rearward end.

In one embodiment, there is provided a plurality of ramp surfaces within the forward portion of the sleeve with the abutments located between the ramp surfaces, and shoulders to each side of each ramp surface. The forward end of each finger is turned to lie on the internal tapering surface so that on subsequent movement of the carrier to its protecting position, each finger slides along the tapered surface and then engages behind the associated abutment.

For the embodiment where the carrier is slidably mounted within the rearward portion of the sleeve, there may be at least one guide extending axially along the inner surface of the rearward portion, the carrier being engageable with the guide thereby to restrain relative axial rotation between the carrier and the sleeve. For the alternative embodiment where the forward portion of the sleeve is slidable with respect to the rearward portion thereof, there should be means to restrain relative rotation between the forward and rearward portions.

In all embodiments of this invention, it is preferred that the initial position of the carrier with respect to the forward portion of the sleeve corresponds axially to the final protecting position thereof where the fingers lock the carrier against movement with respect to said forward portion. By virtue of the action of the locking member, it becomes possible to have identical relative positions for the carrier within the sleeve, at both the initial and final positions. In turn, this allows the fingers to be relatively unstressed at both the initial and final positions so that even with long term storage of the device before use, the fingers will not take a set, so that reliable operation may be expected.

In a preferred embodiment, the carrier has a bore adapted to connect to the hub of a medical needle so that the needle will project forwardly from the carrier when connected thereto. When so connected and the carrier is in its initial position, the needle should be disposed wholly within the sleeve so as to be protected thereby. In an alternative embodiment, the carrier is configured directly to carry the needle itself and so as to serve as a hub for that needle, connectable to a syringe.

This invention extends to a safety needle assembly comprising a safety device of this invention as described immediately above in combination with a medical needle having a hub and received in the bore of the carrier. In the alternative, this invention extends to a safety needle assembly comprising a safety device of this invention and wherein a medical needle is secured to the carrier so as to project forwardly therefrom.

By way of example only, certain specific embodiments of safety devices of this invention will now be described in detail, reference being made to the accompanying drawings in which.

Referring initially to FIGS. 1 to 6 of the drawings, there is shown a safety device 10 for a medical needle 11 intended for use in conjunction with a syringe (not shown) to permit the performance of an injection procedure, to dispense a liquid drug into a human or animal body. The safety device 10 serves to give passive protection for a clinician or other operator—that is to say, the needle 10 is covered by a sleeve prior to the performance of the procedure, is exposed automatically as the procedure is performed, and is automatically covered once more at the completion of the procedure. Moreover, following the completion of the procedure, the sleeve which covers the needle is locked in its protecting position so that the needle may not be used for a second time.

The syringe may be entirely conventional, having a barrel fitted with a plunger which projects from the rear end of the barrel, the plunger having a piston which is a close sliding fit within the barrel to permit the dispensing of a liquid medicament through a mount provided at the forward end of the barrel. The external surface of the mount is typically profiled appropriately for the connection of a needle hub thereto—for example by means of a Luer taper lock though other needle connection systems could be employed.

The safety device 10 is adapted for mounting on the hub 12 of a needle 11, to serve as an accessory to confer protection against accidental injury to a clinician using the syringe to perform an injection. The device comprises a carrier 14 having a bore 15 within which is received the needle hub 12. The needle hub has a circumferential rib 16 which is received in a corresponding groove in the bore 15 of the carrier, the rib and groove being profiled such that it is relatively easy to snap-fit together the carrier and hub, but when fitted together, it is very difficult to separate the two components. The carrier includes a flange 17 having a peripheral lip 18, three axial slots 19 being formed around the periphery of the lip for a purpose to be described below. The forward end of the carrier is formed as a tube 20 which surrounds the rear part of the needle. Four slots 21 (only one of which is visible in FIG. 3) are provided in the carrier to receive respective vanes 22 formed on the needle hub 12.

Figures 2, 3:
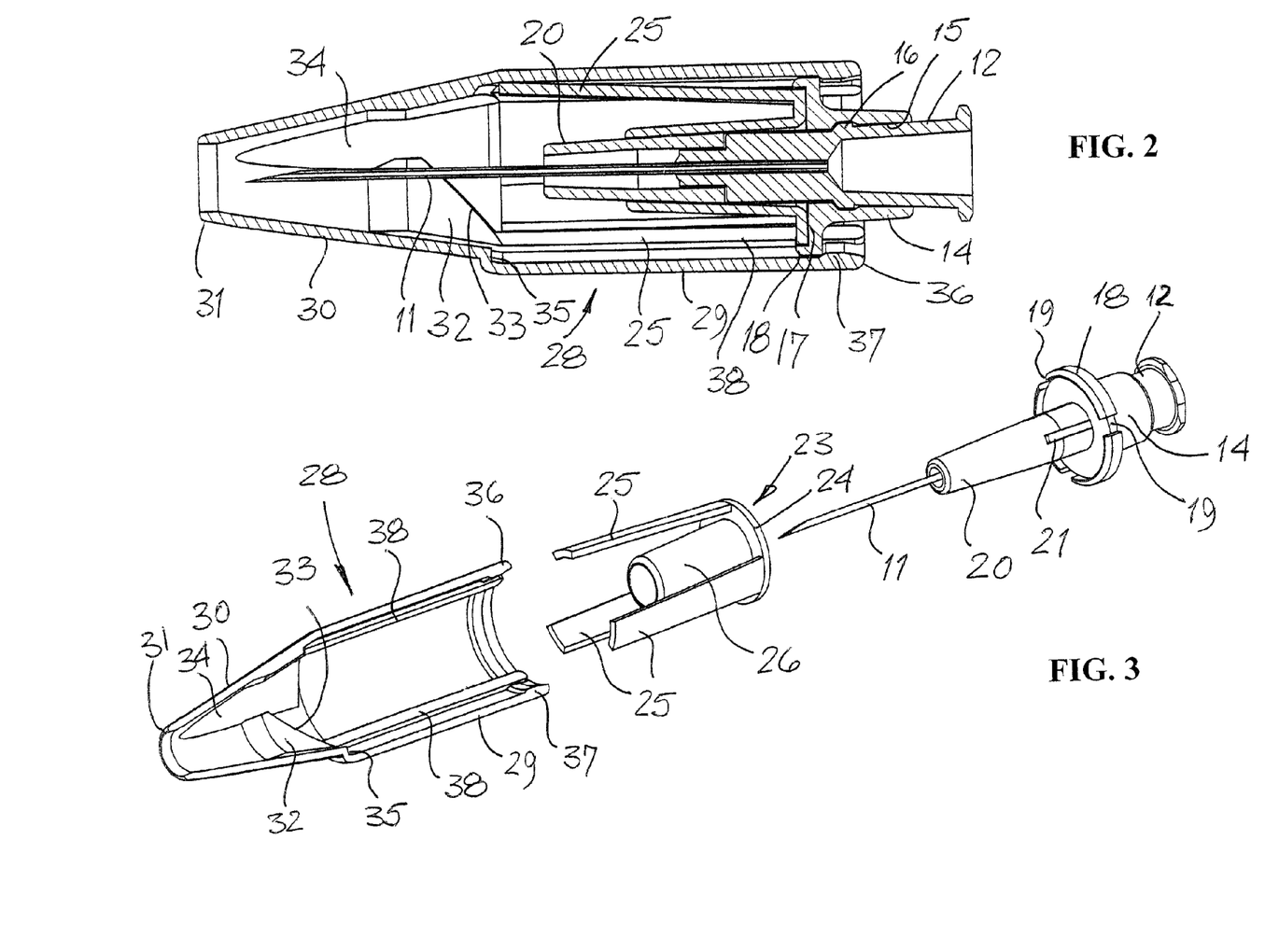
FIG. 2 is an axial cross-section through the device of FIG. 1, in the initial setting.
FIG. 3 is an isometric exploded view of the device.
Figure 4:
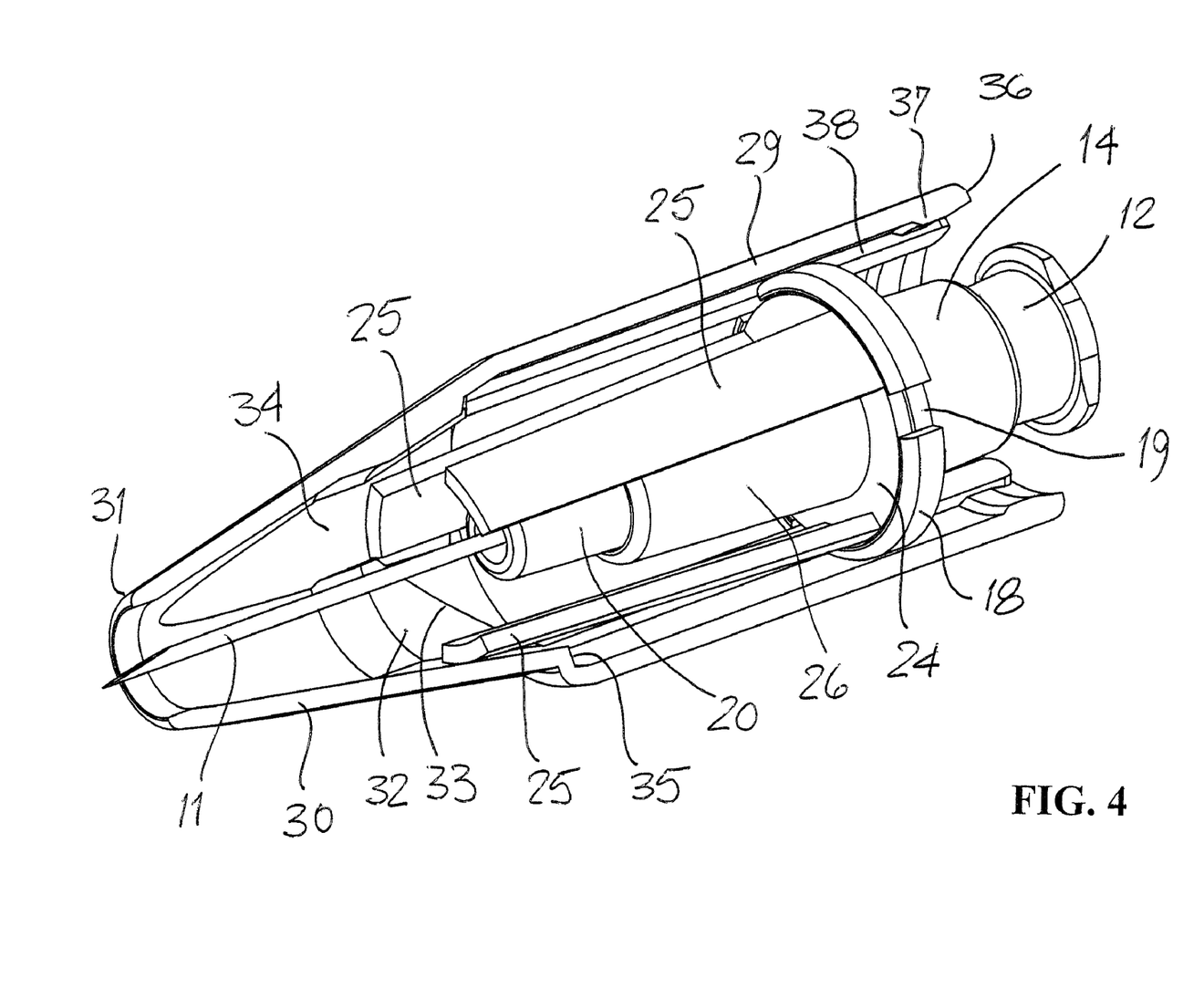
FIG. 4 is a view similar to that of FIG. 1, but with the device partway through an operating cycle from the initial setting of FIG. 1.

A locking member 23 is mounted on the carrier 14 and as best seen in FIG. 3, has a circular base plate 24 which is received against the flange 17 of the carrier, within the lip 18. Three resilient fingers 25 project forwardly from the periphery of the base plate and flare outwardly therefrom, the fingers 25 being resiliently deformable inwardly towards the axis of the locking member. A hollow central boss 26 is provided on the base plate 21 and receives the forward part of the needle hub 12 when assembled therewith, tube 20 projecting beyond the forward end of the boss 26.

The safety device further comprises an outer sleeve 28 having a generally cylindrical rearward portion 29 and a forward portion 30 which tapers both internally and externally towards its forward end 31 from its junction with the cylindrical rearward portion 29. Internally within the forward portion 30 there are three lands 32 projecting towards the axis of the sleeve 28, each land having a cam surface 33 extending essentially helically within the forward portion 28. In the region of those lands 32, there is a generally smooth transfer from the internal wall of the cylindrical rearward portion 29 to the internal surface of the forward portion, but between each pair of lands 32, the internal tapering wall of the forward portion provides a step-like abutment 35 between the internal walls of the rearward and forward portions respectively.

Figure 1:
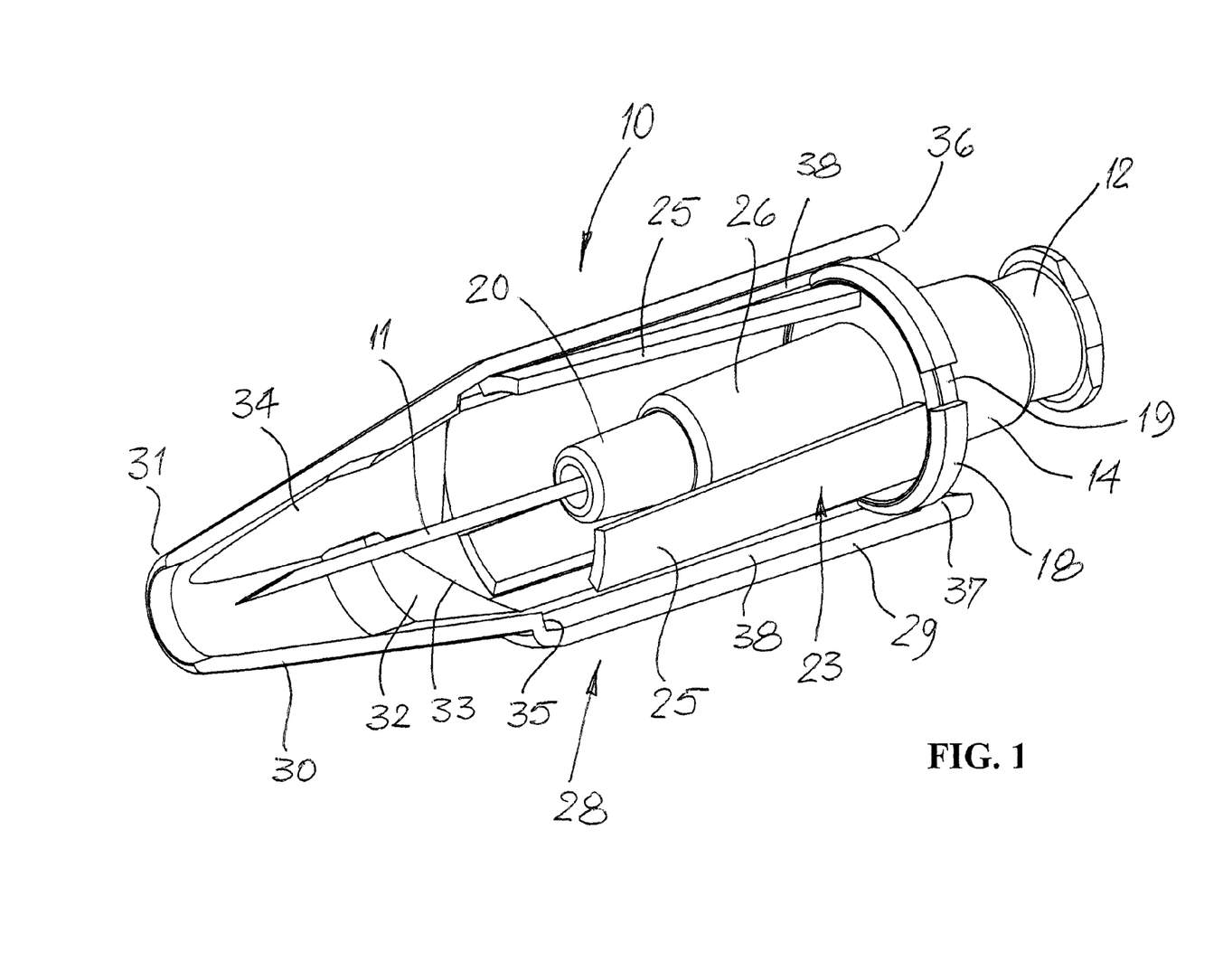
FIG. 1 is a partly cut-away view of the first embodiment of safety device for use with a medical needle, shown connected to a needle having a needle hub for connection to a syringe, with the device in an initial setting.

The sleeve 28 is slidably mounted on the periphery of the lip 18 of the carrier 14, the open rearward end 36 of the sleeve rearward portion 27 having an internal rib 37 which is snap-fitted over the carrier so as thereafter to retain the carrier within the bore of the rearward portion. Three upstanding axially-extending guides 38 are provided within the bore of the rearward portion 27, the slots 19 in the carrier 14 running on those guides thereby to prevent relative rotation between the carrier and the sleeve. As shown in FIGS. 1 and 2, with the carrier in its fully rearward position abutting the rib 37, the fingers 25 fit wholly within the rearward portion 29 of the outer sleeve with the forward ends of the fingers closely adjacent the junction between the rearward and forward portions of the sleeve. These figures show the initial setting of the device, with the fingers aligned with the lands 32 and with a needle 11 positioned within the device, the hub 12 thereof being engaged with the carrier 14. As shown, the needle 11 lies wholly within the outer sleeve 28.

When a medical procedure is to be performed, the safety device 10 having the needle 11 located with the carrier 14 is connected to a syringe pre-charged with medicament by coupling the Luer taper socket of the needle hub 12 to the Luer taper spigot at the forward end of the syringe. The safety device 10 is in its initial position shown in FIG. 1, ready for use.

On commencing the procedure, the forward end 31 of the forward portion 30 of the outer sleeve 28 is pressed into engagement with the skin of a patient and forward pressure on the syringe (not shown) slides the carrier 14 together with the locking member 23 and needle 11 forwardly such that the needle starts to project from the forward end 31 of the sleeve 28. During this initial movement, the forward ends of the fingers 25 ride on to the forward portion 30 of the outer sleeve and contact the cam surfaces 33 of the lands 32, thereby causing the locking member 23 to rotate to the position shown in FIG. 4. Here, the forward ends of the fingers 25 have been moved to lie wholly upon the surfaces 34, but in so doing, the fingers 25 have moved closer to the axis of the outer sleeve by virtue of the taper of the forward portion of the outer sleeve. That movement of the fingers is against their resilient bias and so generates an axial rearward force on the locking member and so too on the carrier, urging the carrier back towards its initial position.

Figure 5:
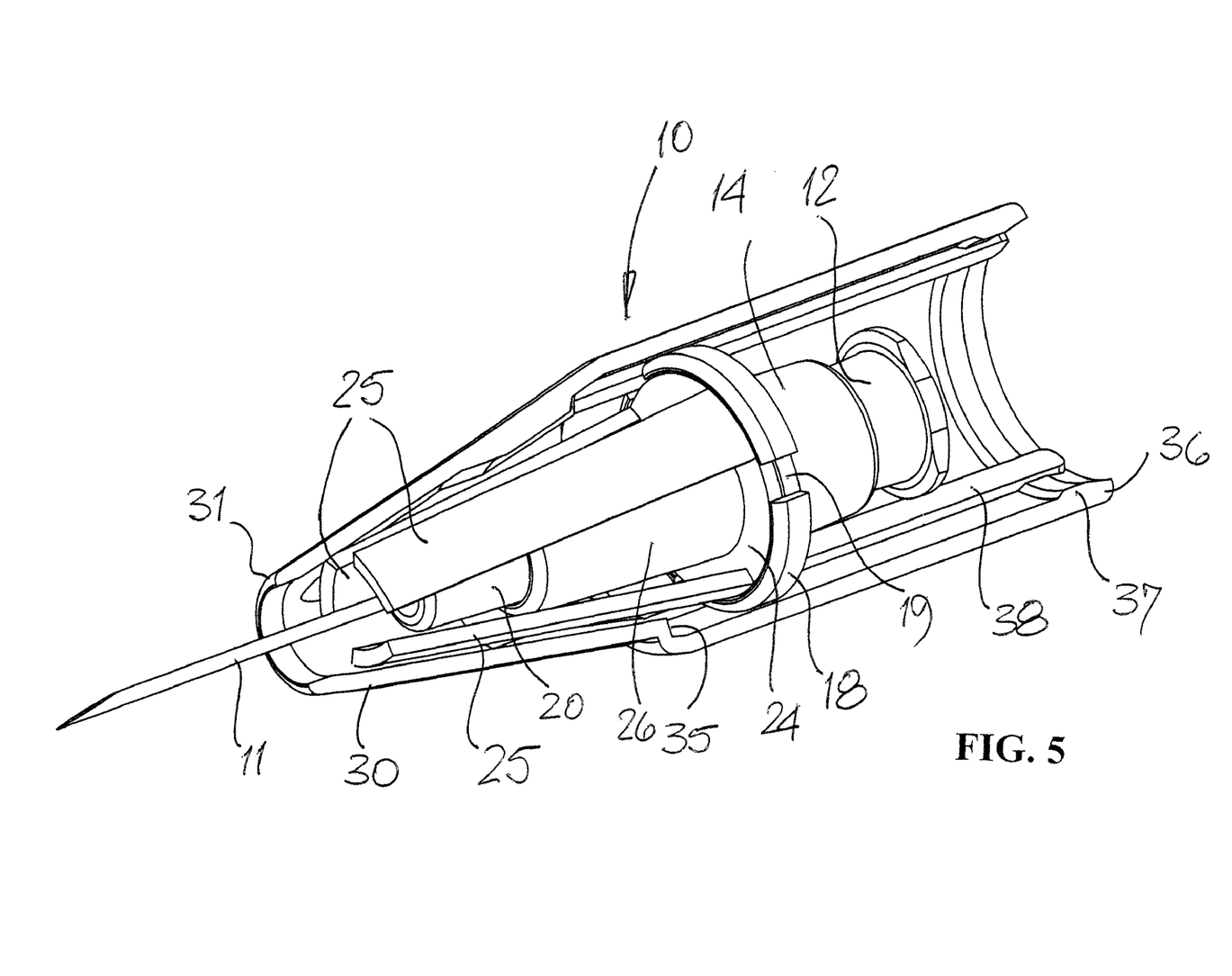
FIG. 5 is a further view of the device but with the needle projecting fully therefrom.
Figure 6:
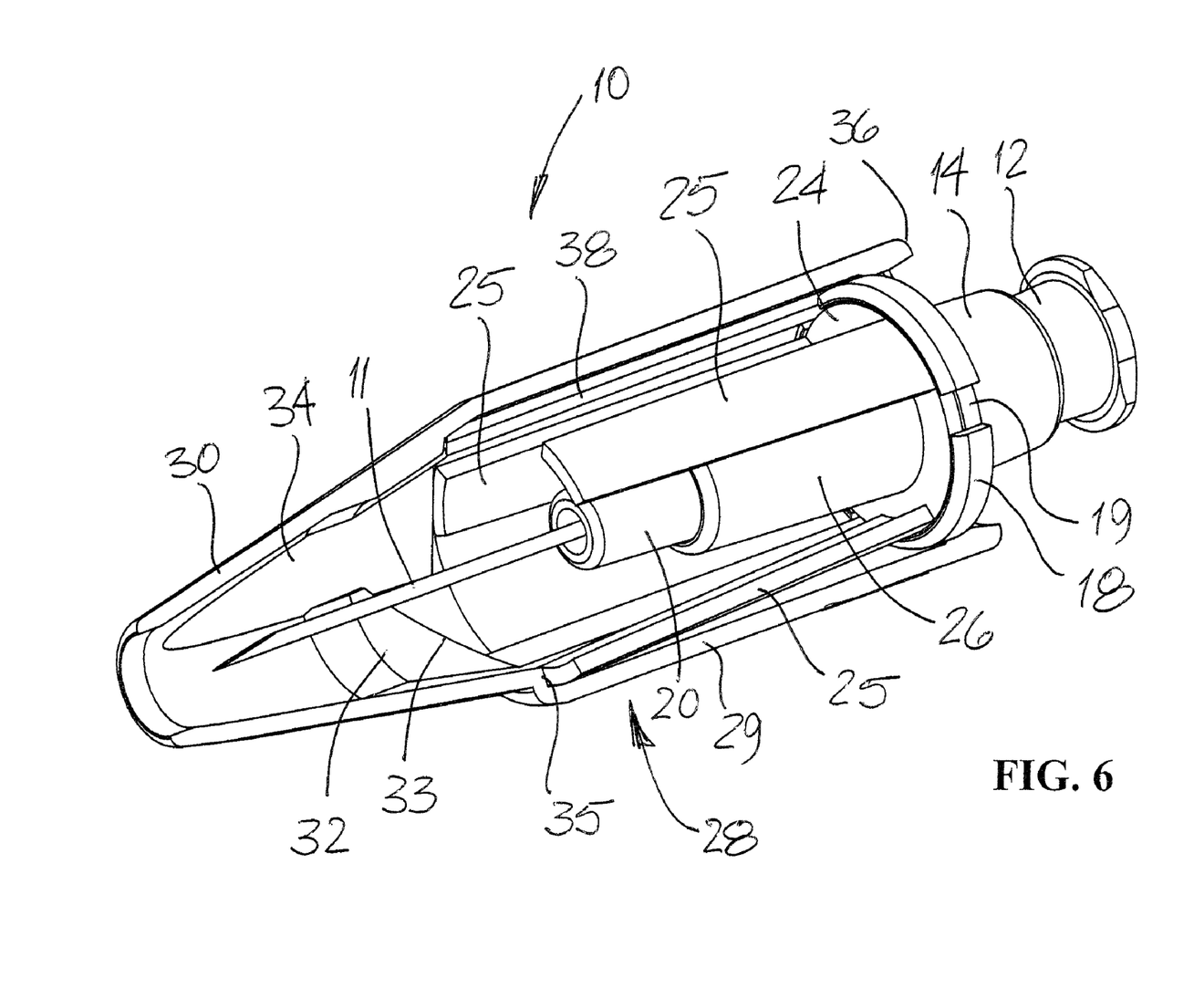
FIG. 6 shows the device at the completion of a procedure, with the outer sleeve locked in its final protecting position.
Figure 7:
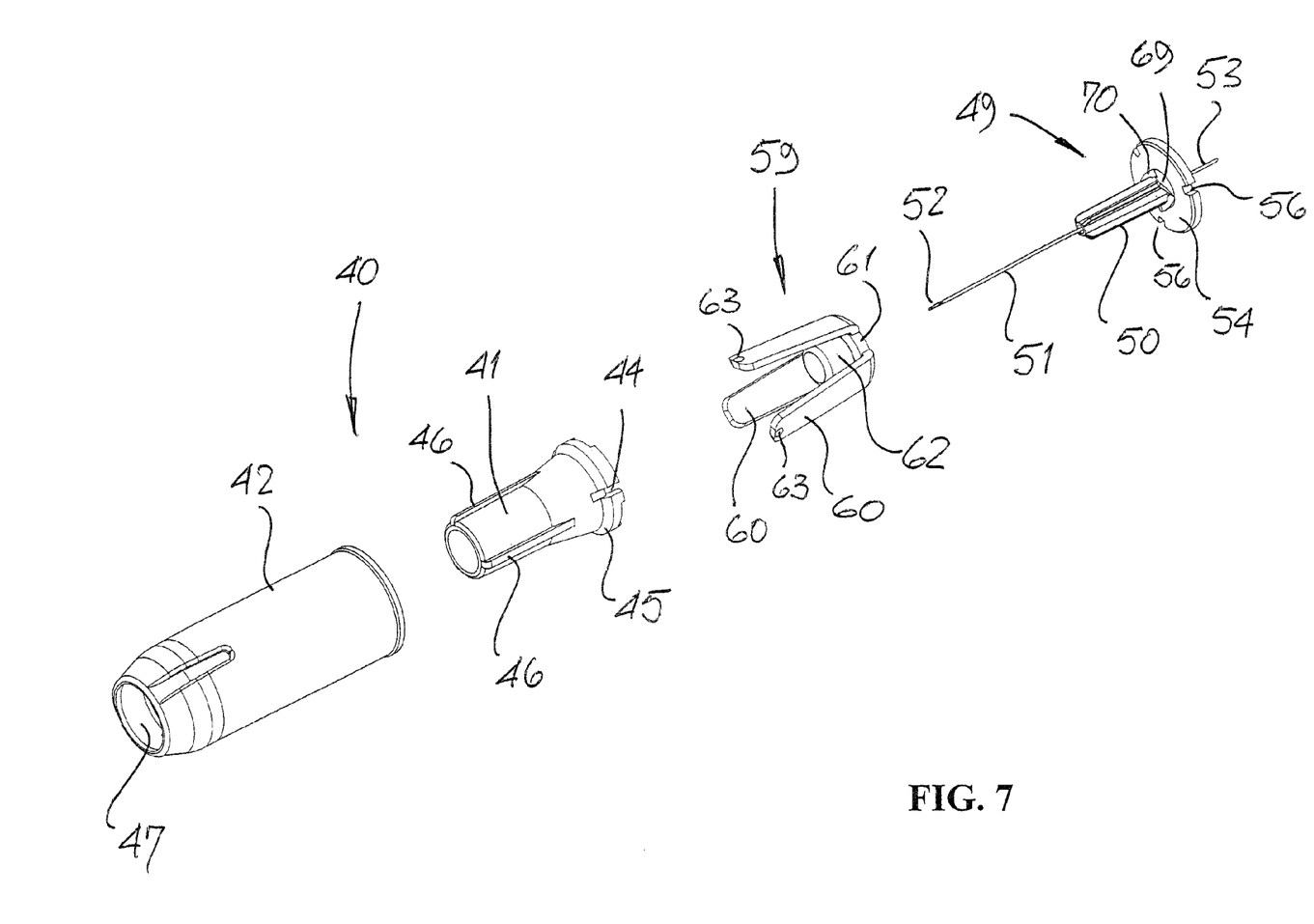
FIG. 7 is an exploded isometric view of a second embodiment, which includes a needle integral with the carrier.
Figure 8:
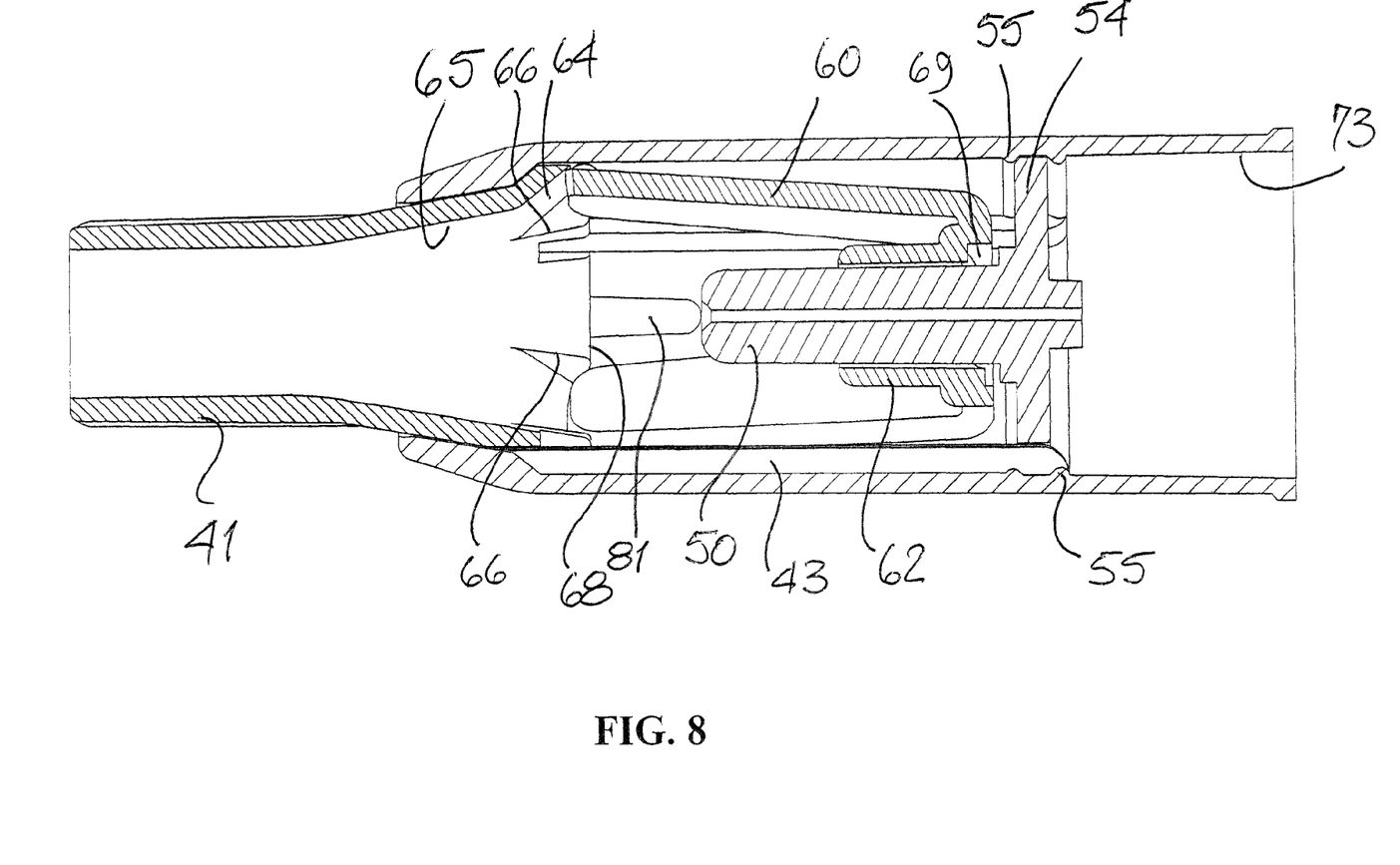
FIG. 8 is an axial section of the device of FIG. 7 but with the needle removed for clarity.
Figures 9, 10:
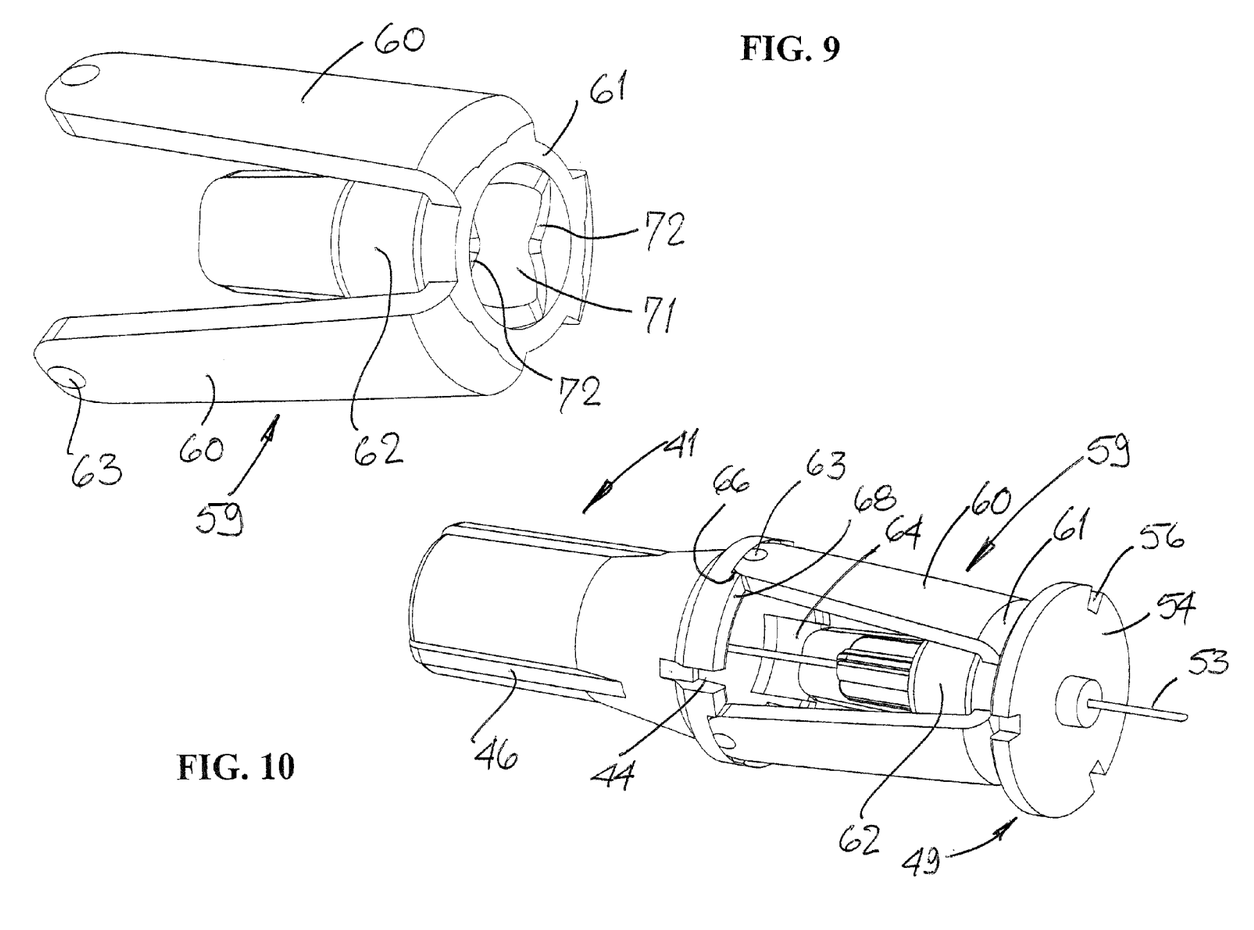
FIG. 9 is a rear isometric view of the locking member, showing the internal cam profile.
FIG. 10 is a view on the needle carrier, locking member and forward portion of the sleeve of the second embodiment.
Figure 11:
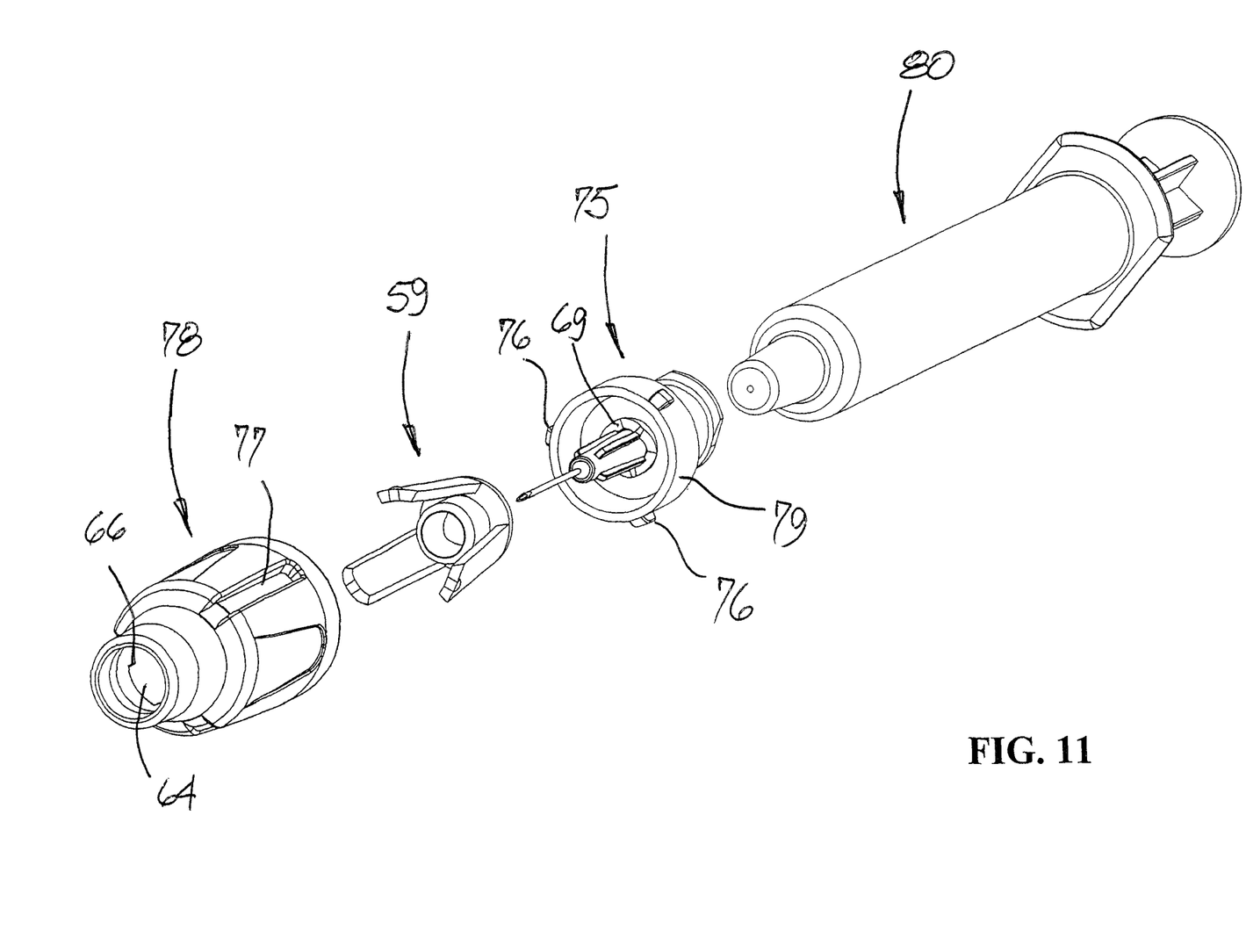
FIG. 11 is an exploded isometric view of a third embodiment, shown with a syringe and a needle separable from the device.
Figure 12A:
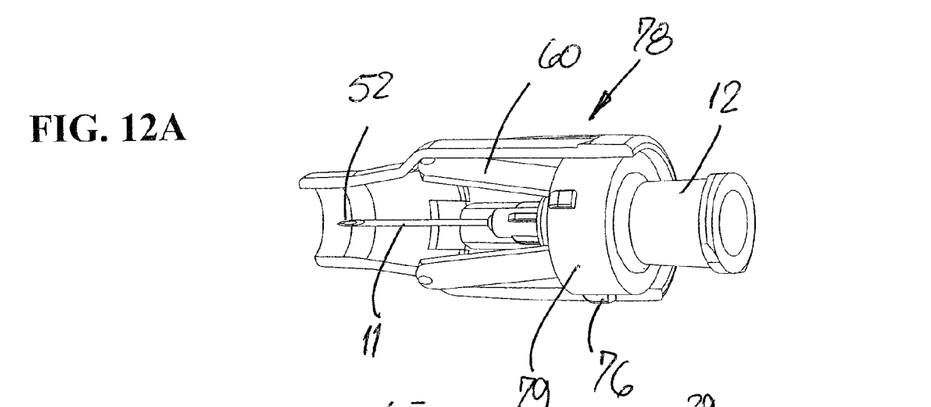
FIGS. 12A, 12B, 12C and 12D show the device of FIG. 11 fully assembled with a needle, during four stages of operation.
Figures 12B, 12C:
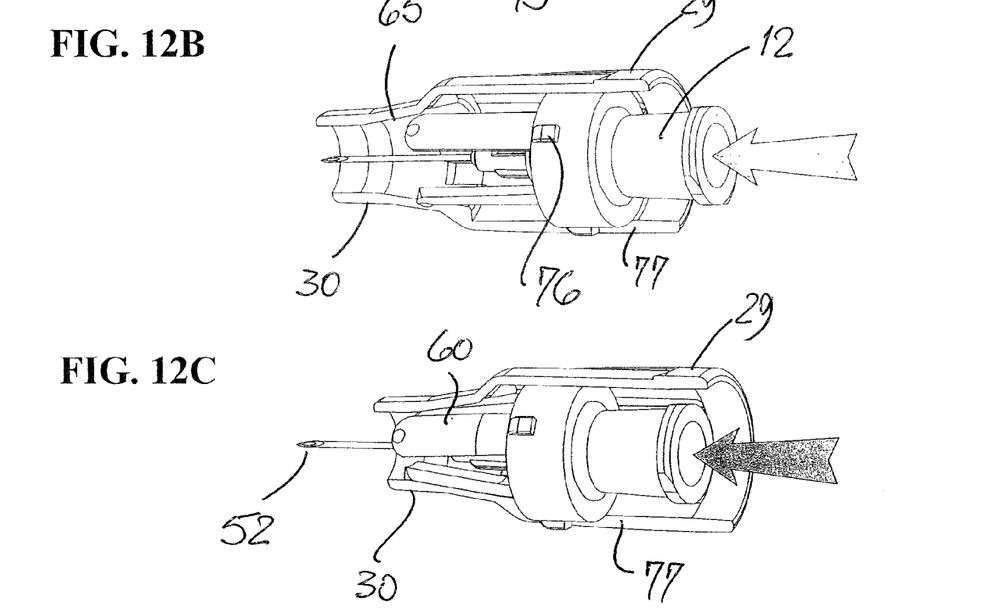
Figure 12D:
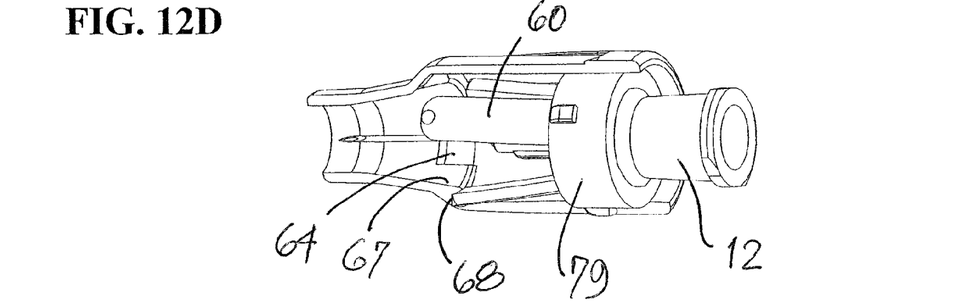

The medical procedure may continue until the carrier, locking member and needle are all fully forward, as shown in FIG. 5. Here, the forward ends of the fingers 25 have been moved resiliently to be close to the axis of the outer sleeve and so generate the greatest axially rearward restoring force on the carrier. At the completion of the procedure, the syringe is withdrawn from the patient, so pulling the carrier and needle rearwardly, the restoring force generated by the fingers 25 serving to push the outer sleeve forwardly to remain in contact with the skin of the patient until the needle is fully withdrawn into the sleeve. As this occurs, the fingers drop off the respective surfaces 34, so as to lie behind the respective abutments 35 (FIG. 6). When in this position, the forward ends of the fingers are trapped behind the abutments and so resist forward movement of the locking member, carrier and needle.

It will be appreciated that when the carrier is locked in the position shown in FIG. 6, with the forward ends of the fingers engaging the abutments 35, the carrier is in the same axial position with respect to the sleeve 28 as it was in, before the safety device had been used. In view of this, the sleeve 28 may be made as short as is necessary wholly to protect the needle and no extra allowance need be provided to accommodate axially distinct initial and final protecting positions.

FIGS. 7 to 10 show a second embodiment of device of this invention differing from that of FIGS. 1 to 6 in that the outer sleeve 40 has forward and rearward portions 41 and 42 with portion 42 slidably mounted within rearward portion 42, for movement along the axis of the outer sleeve. Internally, the rearward portion 42 is provided with three ribs 43 which locate in corresponding slots 44 in a flange 45 formed at the rearward end of the forward portion 41, whereby the forward and rearward portions are held against relative rotational movement. The forward portion has external splines 46 which are a sliding fit within hole 47 at the forward end of the rearward portion 42, whereby the forward and rearward portions are held coaxial notwithstanding relative sliding movement therebetween.

A needle carrier 49 has a central hub 50 in which is mounted a needle 51 having a sharp tip 52 at its forward end and a rearward extension 53. The needle carrier is mounted in the rearward portion 42 of the sleeve 40 by means of a disc 54 is formed integrally with the hub 50. The periphery of the disc locates between two internal circumferential ridges 55 in the rearward portion 42 to hold the carrier 49 against axial movement. Three notches 56 are formed in the periphery of the disc to accommodate the axial ribs 43 within the rearward portion 42.

There is provided a locking member 59 generally similar to that of the first embodiment and so including three fingers 60 projecting forwardly from a base plate 61 having a hollow central boss 62 by means of which the locking member is slidably mounted on the hub 50 of the needle carrier 49. Each finger has a rounded outwardly directed protrusion 63 at its forward end, to minimise friction between the finger and the surfaces over which that finger slides.

Internally, the rearward end of forward portion 41 of the sleeve 40 is formed with three ramp surfaces 64, one for each finger, to guide each finger on to the internal main conical surface 65 of portion 41. To each side of each ramp surface 64 there is provided a shoulder 66 which resists rotational movement of the locking member 59; on the forward portion 41 moving rearwardly into the rearward portion 42, the fingers ride up the ramp surfaces 64 and onto the main conical surface 65, and the locking member is thereafter free to rotate. The conical surface 65 extends rearwardly to each side of each ramp surface 64 and an abutment 68, corresponding to abutment 35 of the first embodiment.

Figure 14A:
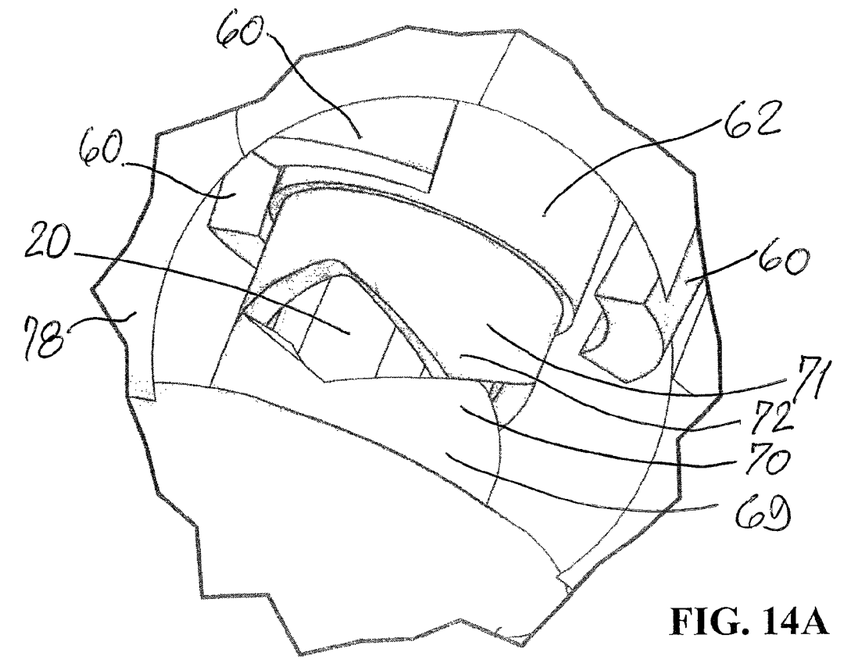
FIGS. 14A and 14B are detail views on an enlarged scale of the rearward cut away part of the device of FIG. 11, respectively in the initial setting of FIG. 12A and in the subsequent setting of FIG. 12B.
Figure 14B:
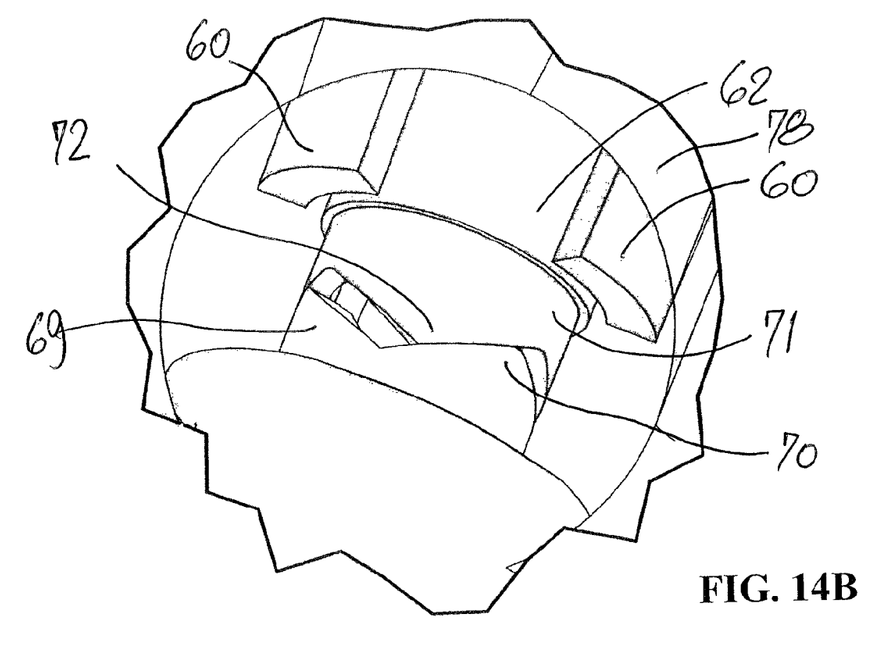
Figure 15:
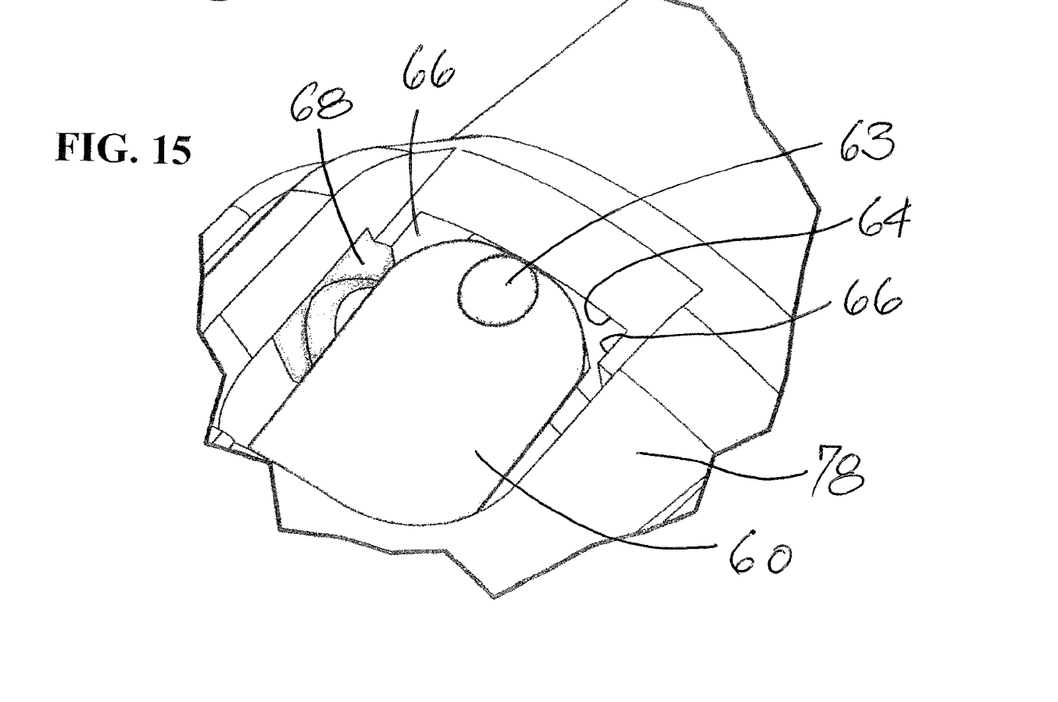
FIG. 15 is a detail view on an enlarged scale of the forward cut away part of the device of FIG. 13, in the initial setting of FIG. 13.

At the junction between hub 50 and disc 54 of the needle carrier 49, there is formed a cylindrical cam surface 69 having two lobes 70 (best seen in FIGS. 14A and 14B, illustrating the third embodiment to be described below). Internally within the base plate 61 of the locking member 59 and facing rearwardly, there is a further cylindrical cam surface 71 having two lobes 72 the profile of which correspond to those of cam surface 69. Relative rotational movement between the needle carrier 49 and locking member 59 will result in relative axial movement between these components so long as the locking member remains in axial engagement with the needle carrier.

The internal configuration of the forward and rearward portions 41 and 42 of the outer sleeve, the needle carrier 49 and the locking member 59 is such that when first assembled into its set position, the disc 54 is relatively separated from the base plate 61, with the lobes of the respective cam surfaces ridden up one another, as best seen in FIG. 14A mentioned above. The locking member is restrained against rotation by virtue of the shoulders 66 of the ramp surfaces 64 and the carrier 49 and forward portion 41 are restrained against rotation relative to one another by virtue of the ribs 43 extending internally within the rearward portion 42.

The device is used in the same manner as has been described above with respect to FIGS. 1 to 7, except that this device is intended for use as an accessory to a pen injector (not shown), the forward end of which is received in bore 73 in the rearward portion 42 of the outer sleeve 40, the rearward extension of the needle 51 then penetrating a bung of a cartridge of medicament contained within the injector. On performing an injection, the injector carrying the device is offered to an injection site and then pressed forwardly, so moving the rearward portion 42 forwardly with respect to the forward portion 41 to expose the needle and permit the performance of the injection procedure. The forward portion 41 moves rearwardly relative to locking member 59 such that the fingers 60 ride up the ramp surfaces 64, by virtue of the axial pressure on the locking member imparted thereto by the needle carrier 49. This axial pressure applies a rotational torque to the locking member 59, through the respective cam surfaces 69,71 but the locking member is restrained against rotation by shoulders 66 until the fingers 60 come clear of the ramp surfaces 64.

Once the fingers are on the main conical surface 65, the locking member is free to rotate and is turned by the interengagement of the cam surfaces 69,71. On completion of the injection procedure, the injector is moved away from the injection site and the forward portion 41 moves forwardly under the spring restoring force provided by the fingers 60 of the locking member 59. The forward ends of the fingers 60 move along the conical surface and drop behind the abutments 68, thereafter blocking movement of the forward portion 41 rearwardly, as has been described above with reference to the first embodiment.

FIGS. 11 to 15 show a third embodiment of device of this invention, differing from the first embodiment in that instead of having cam surfaces 33 within forward portion 30 of the outer sleeve 28, cam surfaces are formed between the needle carrier and rearward end of the locking member, as has been described above with reference to FIGS. 7 to 10 showing the second embodiment. As such, components having a like function to those of the first and second embodiments are given like reference characters and will not be described in detail again, in the following.

As compared to the first embodiment, the needle carrier 75 of this third embodiment has lugs 76 which engage in slots 77 in the outer sleeve 78, to resist relative rotation therebetween. The lugs 76 are provided on a cylindrical surface 79 which is a sliding fit within the sleeve 78 and internally, the carrier is provided with a cylindrical cam surface 69 having two forwardly directed lobes 70. The locking member 59 is essentially identical to that of the second embodiment and so has a further cam surface 71 for engagement with cam surface 69.

The internal formation of the conical forward portion of sleeve 78 is as has been described with reference to the second embodiment and so includes ramp surfaces 64, an internal main conical surface 65 and abutments 68.

Figure 13:
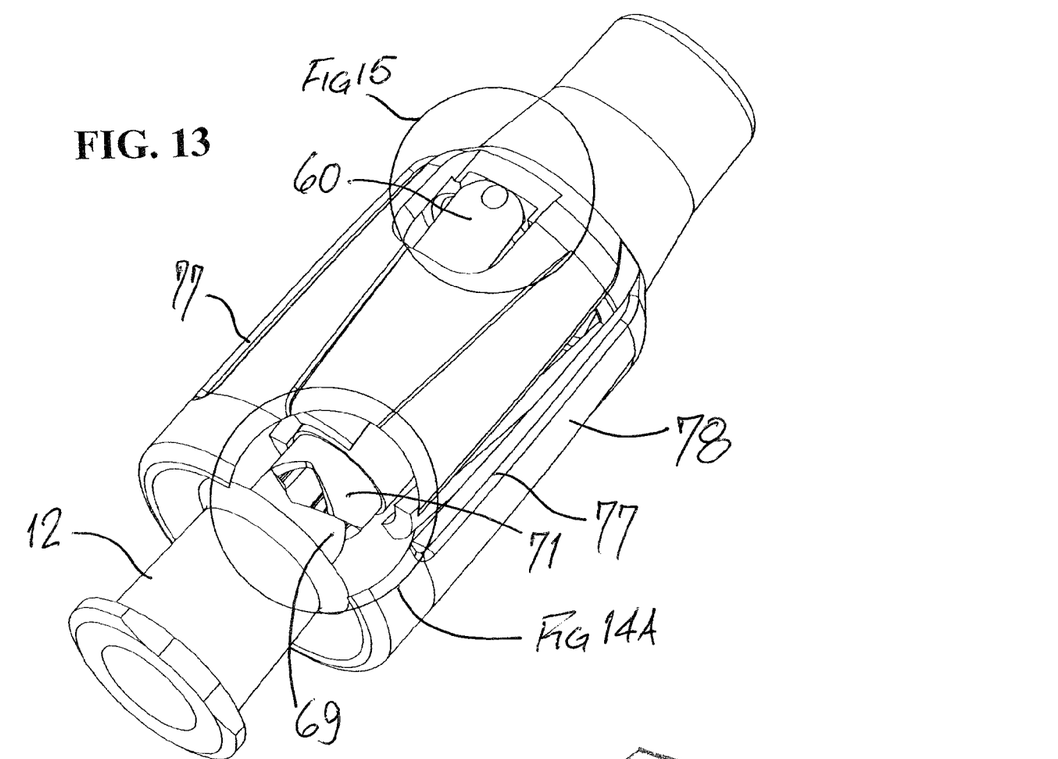
FIG. 13 is a partly cut away view of the device of FIGS. 11 and 12.

An injection procedure is performed by mounting a needle hub 12 in the carrier 75 so that the sharp tip of the needle 11 projects forwardly from the carrier, and the hub 12 is connected to the Luer spigot at the forward end of a conventional syringe 80. The initial relative disposition of the components of the device is as described above for the second embodiment and thus the cam surfaces 69 and 71 are as shown in FIGS. 13, 14A and 14B. On moving the needle carrier 75 forwardly with respect to the sleeve 78, the forward ends of the fingers ride up the ramp surfaces 64 and on to the main conical surface 65; initially, the cam surfaces 69,71 have the relative disposition shown in FIG. 14A but on the forward ends of the fingers moving on to the main conical surface, the locking member becomes free to rotate and so is rotated by the interengaged cam surfaces, to take up the position shown in FIG. 14B. On completion of the procedure, the sleeve 78 is moved forwardly under the restoring force provided by the fingers of the locking member, until the fingers drop behind the abutments 68 and so block the sleeve 78 from rearward movement once more, relative to the needle carrier 75.

With any of the above embodiments, there may be provided a visual indication that the device has been used and so relative movement between the carrier and forward portion of the sleeve is blocked. This may be achieved by providing one or more slots in the sleeve through which a finger or the fingers may be observed when the locking member has been turned from its initial position. Such a slot is shown at 81, marked on FIG. 8. Visibility of the fingers through the slots may be improved by appropriate colouring of the fingers.

The invention claimed is:

1. A safety device for a medical needle having a sharp tip, which device comprises:
   an outer sleeve having an internal surface including a forward portion which tapers internally towards its forward end and a rearward portion defining an essentially parallel bore;
   a carrier for a needle supported in the bore and arranged for axial movement with respect to the forward portion of the sleeve, the carrier and forward portion having an initial position where at least the tip of the supported needle is surrounded by the forward portion and further having an injecting position where the supported needle projects from the forward portion;
   a locking member forwardly of the carrier and also arranged for axial movement with respect to the forward portion of the sleeve, the locking member having at least one resilient finger projecting forwardly within the sleeve, the locking member and forward portion also having an initial relative position where the forward end of the finger contacts the inner surface of the sleeve in the region of the junction between the forward and rearward portions thereof and on relative movement of the locking member and forward portion from their initial position, the finger is resiliently deformed inwardly thereby urging the locking member and carrier back to their initial positions;
   at least one abutment formed between the forward and rearward portions of the sleeve, which abutment is out of angular alignment with the finger when the locking member and forward portion are in their initial position; and
   control means for turning the locking member during relative movement between the carrier and the forward portion from their initial position thereby bringing the forward end of the finger onto the tapering internal surface of the forward portion and into angular alignment with the abutment, such that when the carrier and forward portion return to their initial position, the forward end of the finger locates behind the abutment and so blocks subsequent movement.

2. The safety device as claimed in claim 1, wherein the outer sleeve is generally tubular with a substantially cylindrical rearward portion merging into a substantially conical forward portion.

3. The safety device as claimed in claim 2, wherein the carrier is mounted within the rearward portion of the sleeve for sliding movement with respect thereto along the axis of the sleeve.

4. The safety device as claimed in claim 1, wherein the forward portion of the sleeve is slidably mounted within the rearward portion, the carrier being mounted within the rearward portion and restrained against movement with respect thereto.

5. The safety device as claimed in claim 3, wherein the control means includes a first cam surface formed within the sleeve and engageable by a second cam surface provided on the finger, one of each first and second cam surfaces extending generally helically with respect to the axis of the sleeve whereby interaction between the first and second cam surfaces on movement of the locking member forwardly from its initial position with respect to the forward portion turns the locking member about the sleeve axis.

6. The safety device as claimed in claim 5, wherein the first cam surface is formed within the forward portion of the sleeve and the second cam surface is defined by the forward end of the finger.

7. The safety device as claimed in claim 5, wherein the axial spacing of the first and second cam surfaces when the locking member and forward portion are in their initial position is set to a pre-determined distance such that the locking member may move with respect to the forward portion through said pre-determined distance from its initial position and back thereto without the locking member being rotated.

8. The safety device as claimed in claim 3, wherein the abutment is formed at the rearward end of the internal tapering surface of the forward portion so that on movement of the carrier back to its initial position, the finger slides along the internal surface of the forward portion and then locates behind the associated abutment.

9. The safety device as claimed in claim 1, wherein the control means comprises interacting cam surfaces provided respectively on the carrier and the locking member and arranged to cause rotation of the locking member with respect to the carrier on forward movement of the carrier with respect to the locking member.

10. The safety device as claimed in claim 9, wherein the carrier has a forward-facing surface confronting a rearward-facing surface of the locking member, said interacting cam surfaces being provided on the forward- and rearward-facing surfaces.

11. The safety device as claimed in claim 10, wherein the rearward-facing surface of the locking member is formed at the rearward end of the locking member and the finger projects forwardly from that rearward end.

12. The safety device as claimed in claim 3, wherein there is at least one guide formed internally within the rearward portion of the outer sleeve and extending substantially parallel to the sleeve axis, the carrier being engageable with the guide thereby to restrain relative axial rotation between the carrier and sleeve.

13. The safety device as claimed in claim 1, wherein a ramp surface is provided to guide the forward end of the finger on to the internal tapering surface of the forward portion, a shoulder is provided to each side of the ramp surface and is engageable by the forward end of the finger, to resist rotation of the locking member.

14. The safety device as claimed in claim 1, wherein there is a plurality of fingers equi-spaced around the axis of the sleeve, and a like plurality of abutments, one of said abutments being associated with each finger.

15. The safety device as claimed in claim 14, wherein the locking member has three fingers and in the initial position of the locking member, the forward ends of the fingers engage the internal surface of the rearward portion of the outer sleeve.

16. The safety device as claimed in claim 15, wherein the final relative position of the carrier and forward portion of the sleeve is substantially the same as the initial relative position of the carrier and forward portion.

17. The safety device as claimed in claim 1, wherein the carrier has a bore adapted to connect to a hub of a medical needle, whereby a needle connected to the carrier projects forwardly therefrom, the needle being disposed wholly within the sleeve when the carrier is in its initial position.

18. The safety device as claimed in claim 17, wherein the bore in the carrier is formed with one of a rib and groove adapted to co-operate with a corresponding groove and rib respectively, formed on the external surface of the needle hub.

19. The safety device as claimed in claim 18, wherein the rib and groove are profiled to facilitate entry of the rib into the groove but to resist withdrawal of the rib from the groove, once entered.

20. The safety needle assembly comprising the safety device as claimed in claim 18 in combination with a medical needle having a hub received in the bore of the carrier.

21. The safety needle assembly comprising the safety device as claimed in claim 1, wherein a medical needle is secured to the carrier so as to project forwardly therefrom.

22. The safety needle assembly as claimed in claim 21, wherein the carrier has a bore formed to permit connection of the assembly to an injection device.

23. An injection device comprising a cylinder provided with a plunger having a piston furnished at the forward end thereof, and the safety device as claimed in claim 22 fitted to the forward end of the cylinder.

24. An injection device comprising a cylinder, a plunger slidably mounted in the cylinder and having a forward end disposed within the cylinder, a piston furnished at the forward end of the plunger, and the safety needle assembly as claimed in claim 20, the hub of the needle being fitted to the forward end of the cylinder and the carrier of the safety device being connected to the hub of the needle.

* * * * *